United States Patent
Ridvan et al.

(10) Patent No.: US 7,709,662 B2
(45) Date of Patent: May 4, 2010

(54) METHOD OF MANUFACTURING (S)-N-METHYL-3-(1-NAPHTHYLOXY)-3-(2-THIENYL)PROPYLAMINE HYDROCHLORIDE (DULOXETINE)

(75) Inventors: Ludek Ridvan, Prague (CZ); Petr Hruby, Prague (CZ); Lukas Placek, Bruntal (CZ); Miroslav Kuchar, Prague (CZ)

(73) Assignee: Zentiva k.s., Prague (CZ)

( * ) Notice: Subject to any disclaimer, the term of this patent is extended or adjusted under 35 U.S.C. 154(b) by 545 days.

(21) Appl. No.: 11/718,042

(22) PCT Filed: Oct. 21, 2005

(86) PCT No.: PCT/CZ2005/000079

§ 371 (c)(1),
(2), (4) Date: Apr. 26, 2007

(87) PCT Pub. No.: WO2006/045255

PCT Pub. Date: May 4, 2006

(65) Prior Publication Data

US 2009/0143600 A1 Jun. 4, 2009

(30) Foreign Application Priority Data

Oct. 26, 2004 (CZ) .................. 2004-1072

(51) Int. Cl.
*C07D 333/12* (2006.01)
(52) U.S. Cl. ...................................... 549/75
(58) Field of Classification Search .................. 549/75
See application file for complete search history.

(56) References Cited

U.S. PATENT DOCUMENTS 5,362,886 A 11/1994 Berglund

FOREIGN PATENT DOCUMENTS

| WO | 03 097632 | 11/2003 |
|---|---|---|
| WO | 2004 056795 | 7/2004 |

OTHER PUBLICATIONS

Sorbera, L. A. et al.,"Duloxetine Oxalate", Drugs of the Future, vol. 25, No. 9, pp. 907-916, 2000.

*Primary Examiner*—Taofiq A Solola
(74) *Attorney, Agent, or Firm*—Oblon, Spivak, McClelland, Maier & Neustadt, L.L.P.

(57) ABSTRACT

A method of preparation of (S)-N-methyl-3-(1-naphthyloxy)-3-(2-thienyl)propylamine of formula (I) or its pharmaceutically acceptable salt, in which (RS)-N,N-dimethyl-3-(1-naphthyloxy)-3-(2-thienyl)propylamine of formula (III) is reacted with an optically active acid, after which a crystallization is made of that diastereoisomer which yields, by reaction with an inorganic or organic base, (S)-N,N-dimethyl-3-(1-naphthyloxy)-3-(2-thienyl)propylamine of formula (S)-III, which is then demethylated using alkylchloroformates, followed by a hydrolysis and optional conversion of the compound of formula (I) to its salt.

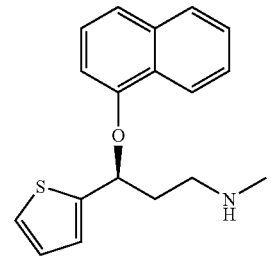

(I)

13 Claims, No Drawings

METHOD OF MANUFACTURING (S)-N-METHYL-3-(1-NAPHTHYLOXY)-3-(2-THIENYL)PROPYLAMINE HYDROCHLORIDE (DULOXETINE)

TECHNICAL FIELD

The invention concerns a new method of manufacturing (S)-N-methyl-3-(1-naphthyloxy)-3-(2-thienyl)propylamine, known under the generic name duloxetine, of formula I

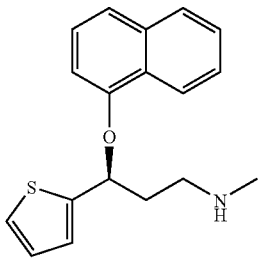

BACKGROUND ART

Duloxetine is a serotonin and noradrenaline reuptake inhibitor, and it has therapeutic use in the fields of depression and urinary incontinence.

Preparation of duloxetine and its intermediate products is described for example in patents EP 0 273 658, U.S. Pat. No. 5,362,886, WO 2004/005239, US 2003/0225153. The basic reaction used is presented in the following Scheme 1.

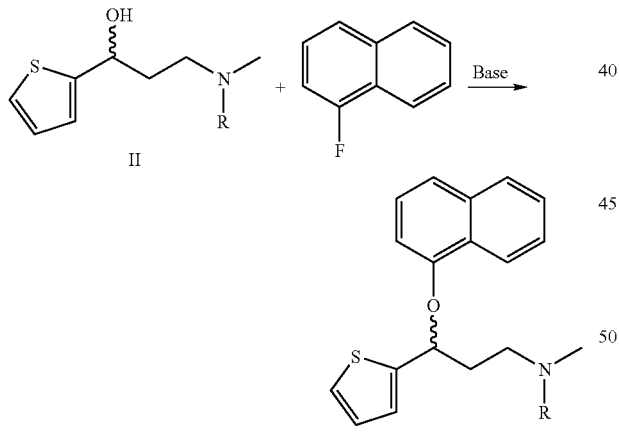

R = H, Me

Most syntheses use the already optically active intermediate product II, i.e. (S)-N,N-dimethyl-3-hydroxy-3-(2-thienyl)propylamine, for this reaction. During synthesis of many optically active compounds, resolving or obtaining optically pure intermediates result in better yields than resolution of the final products. However, with respect to synthesis of duloxetine, it has turned out that during further processing according to Scheme 1, racemization happens again. Thus, the obtained resulting product is not enantiomerically pure and it is necessary to recrystallize it again. This naturally decreases the yield of the process.

A solution of undesirable racemization during the reaction according to Scheme 1 is offered in patent application WO 2004/056795 A1. The authors choose a method of preparation of racemic duloxetine and its resolution with an appropriate chiral acid. Using this procedure, they indeed prevent possible racemization but, on the other hand, they increase losses because they also process the undesired (R)-enantiomer until the final stage.

In the original patents, the reaction according to Scheme 1 was performed under catalysis with strong bases such as sodium hydride or lithium hydride. These bases are relatively expensive and it is necessary to avoid moisture when they are used because they can react with it vigorously.

In the application WO 2004/056795, a method for performing the reaction according to Scheme 1 is also published, wherein the use of a phase-transfer catalyst allows to perform the reaction also with weaker bases such as alkali metal hydroxides.

Preparation of the compound I is described in Example 2 (preparation 2) of U.S. Pat. No. 5,362,886. The final product results from action of concentrated hydrochloric acid on a solution of the duloxetine base in ethyl acetate. An inoculating crystal of compound I is added to the acidified reaction mixture and the mixture is diluted with more ethyl acetate; after stirring for 30 minutes the mixture is again concentrated to the original volume and then stirred at room temperature for 1 hour and at 0° C. for 1 hour.

However, during reproduction of this procedure, it has turned out that the solution starts to turn red during processing, which resulted in a contaminated product. In addition, if the suspension described in U.S. Pat. No. 5,362,886 was to be obtained in the given yield, it was necessary to further prolong the stirring, which resulted in further accumulation of impurities. Experiments using different amounts of hydrochloric acid also were not successful.

The present invention presents a comprehensive solution of manufacture of duloxetine, which eliminates or minimizes all mentioned disadvantages.

DISCLOSURE OF THE INVENTION

The invention relates to a new method of manufacturing (S)-N-methyl-3-(1-naphthyloxy)-3-(2-thienyl)propylamine of formula I

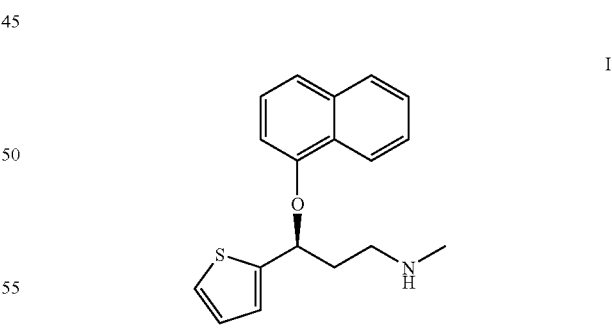

and its pharmaceutically acceptable salts, which comprises resolution of (RS)-N,N-dimethyl-3-(1-naphthyloxy)-3-(2-thienyl)propylamine of formula III by conversion to a mixture of the two diastereoisomers via reaction with an optically active acid, and crystallization of that diastereoisomer which yields, in a reaction with an organic or inorganic base, (S)-N,N-dimethyl-3-(1-naphthyloxy)-3-(2-thienyl)propylamine, which is subsequently demethylated, thus yielding at arising the compound I.

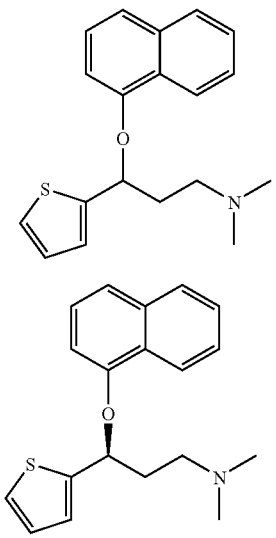

Compound I can be converted to its salts. For example, the oxalate is described, but the hydrochloride is normally used for medical treatment.

It has turned out that (S)-N,N-dimethyl-3-(1-naphthyloxy)-3-(2-thienyl)propylamine ((S)-III) is not racemized in the course of demethylation, which allows to process this optically active intermediate.

In a preferred embodiment optically active D-tartaric acid is used and the diastereoisomer (S)-N,N-dimethyl-3-(naphthyloxy)-3-(2-thienyl)propylamine-D-tartrate is crystallized from cyclic ethers, e.g. tetrahydrofuran, $C_3$ to $C_6$ ketones, e.g. acetone, or lower alcohols, e.g. $C_1$ to $C_3$, preferably methanol or ethanol. (S)-N,N-dimethyl-3-(1-naphthyloxy)-3-(2-thienyl)propylamine of formula (S)-III is released via reaction with a base selected from the group of alkali metal hydroxides or carbonates.

The demethylation itself, during which racemization does not occur, is performed in the solvent mixture of toluene and diisopropylamine at 50 to 110° C., followed by hydrolysis with an alkali metal hydroxide.

Another aspect of the invention includes a method for preparing the starting compound III according to Scheme 1, i.e. via reaction of (RS)-N,N-dimethyl-3-hydroxy-3-(2-thienyl)propylamine with 1-fluoronaphthalene in a solution of dimethylsulfoxide, at temperature of 80 to 150° C. in the presence of a base selected from alkali metal carbonates, hydroxides or alcoholates. This arrangement allows catalysis with a weaker base without using any phase-transfer catalysts.

Another aspect includes preparation of the compound III from the unwanted (R)-N,N-dimethyl-3-(1-naphthyloxy)-3-(2-thienyl)propylamine. This method involves a reaction of this enantiomer with an inorganic or organic base, e.g. tBuOK, sodium methanolate or potassium hydroxide. The reaction is preferably performed in an organic solvent, more preferably in dimethylsulfoxide. After the reaction is completed, the mixture is diluted with water to decompose excess alcoholate and the product is extracted with a non-polar solvent selected from $C_5$ to $C_8$ aliphatic, cyclic or aromatic hydrocarbons, preferably toluene.

The last aspect includes a conversion of the base to the corresponding salt, which is usually performed via reaction with the corresponding acid. As it has turned out, this procedure fails in the case of the most frequently used salt, the hydrochloride. According to the invention, this salt is prepared via reaction of the compound I with a chloride of a weak base, preferably with ammonium chloride.

The invention is further illustrated in the following examples.

EXAMPLES

Example 1

(RS)-N,N-dimethyl-3-(naphthyloxy)-3-(2-thienyl)propylamine-D-tartrate

A mixture of N,N-dimethyl-3-hydroxy-3-(2-thienyl)propylamine (370 g), potassium hydroxide (336 g) and 1-fluoronaphthalene (284 ml) in dimethylsulfoxide (2 l) is stirred at 100° C. for 2 hours. The mixture is then cooled down to lab temperature, diluted with water (4 l) and toluene (2 l). The organic phase is separated, shaken with water and evaporated. A hot solution of D-tartaric acid (252 g) in water (3 l) is added to the evaporation residue under stirring. After cooling down, the precipitated product is sucked off, washed with water and dried. The yield is 687 g (75%).

Example 2

(RS)-N,N-dimethyl-3-(naphthyloxy)-3-(2-thienyl)propylamine

Ground KOH (1.2 g) is added to a solution of (R)-N,N-dimethyl-3-(naphthyloxy)-3-(2-thienyl)propylamine (3.1 g) in DMSO (10 ml), bubbled with a moderate stream of nitrogen, and the mixture is stirred and heated at 100° C. for 1 hour. After cooling down to lab temperature, the mixture is diluted with water (30 ml) and the racemic product is extracted with toluene. After evaporation, 2.6 g (84%) of (RS)-N,N-dimethyl-3-(naphthyloxy)-3-(2-thienyl)propylamine is obtained.

Example 3

(RS)-N,N-dimethyl-3-(naphthyloxy)-3-(2-thienyl)propylamine tBuOK (16.8 g), and 18-crown-6 (0.25 g) are added to a solution of (S)-N,N-dimethyl-3-(naphthyloxy)-3-(2-thienyl)propylamine (31 g) in sulfolane (100 ml), bubbled with a moderate stream of nitrogen, and the mixture is stirred and heated at 110° C. for 2 hours. After cooling down to lab temperature, the mixture is diluted with water (300 ml) and the racemic product is extracted with toluene. After evaporation, 25 g (81%) of RS)-N-methyl-3-(naphthyloxy)-3-(2-thienyl)propylamine is obtained.

Example 4

(RS)-N,N-dimethyl-3-(naphthyloxy)-3-(2-thienyl)propylamine tBuOK (16.8 g) is added to a solution of (R)-N,N-dimethyl-3-(naphthyloxy)-3-(2-thienyl)propylamine (31 g) in DMSO (100 ml), bubbled with a moderate stream of nitrogen, and the mixture is stirred and heated at 110° C. for 2 hours. After cooling down to lab temperature, the mixture is diluted with water (300 ml) and the racemic product is extracted with toluene. After evaporation, 25 g (84%) of (RS)-N-methyl-3-(naphthyloxy)-3-(2-thienyl)propylamine is obtained.

Example 5

(S)-N,N-dimethyl-3-(naphthyloxy)-3-(2-thienyl) propylamine-D-tartrate (RS)-N,N-dimethyl-3-(naphthyloxy)-3-(2-thienyl)propylamine-D-tartrate (461 g) is dissolved in tetrahydrofuran (900 ml) while hot. After cooling down to lab temperature, the mixture is stirred for 24 hours. The precipitated crystals are re-crystallized from tetrahydrofuran (400 ml) once more using the same procedure. The yield is 117 g (25%). Optical purity is 99% ee (CE).

Example 6

(S)-N,N-dimethyl-3-(naphthyloxy)-3-(2-thienyl) propylamine-D-tartrate (RS)-N,N-dimethyl-3-(naphthyloxy)-3-(2-thienyl)propylamine-D-tartrate (461 g) is dissolved in ethanol (700 ml) under reflux. After gradual cooling to lab temperature, the mixture is stirred for 164 hours. The precipitated crystals are sucked off and washed with ethanol. The yield is 150 g (32%). Optical purity is 98% ee (CE).

The crystals are then refluxed in acetone (300 ml). After cooling down to lab temperature the mixture is stirred for 1 h. The crystals are sucked off and washed with acetone. The yield is 140 g (30%). Optical purity is 99.6% ee (CE).

Example 7

(S)-N,N-dimethyl-3-(naphthyloxy)-3-(2-thienyl) propylamine-hydrochloride (Duloxetine)

Diisopropylethylamine (210 ml) is added to a solution of (S)-N,N-dimethyl-3-(1-naphthyloxy)-3-(2-thienyl)-propanamine (311 g; 99.6% ee) in toluene (1200 ml) and then phenylchloroformate (150 ml) is added at 60° C. After stirring at 80° C. for two hours, the mixture is cooled down, shaken with a diluted solution of hydrochloric acid, water and a 2% solution of sodium hydrogencarbonate. The organic phase is dried with sodium sulfate and evaporated. The evaporation residue is dissolved in ethanol (300 ml) and a 5M solution of potassium hydroxide (400 ml) is added drop by drop under reflux. After refluxing for two hours, the mixture is evaporated to half the volume, diluted with water (1,000 ml) and extracted with toluene (300 ml). The organic phase is dried with sodium sulfate and evaporated. The evaporation residue is dissolved in ethanol (300 ml), ammonium chloride is added (80 g) and the mixture is refluxed for two hours. The mixture is then evaporated to dryness, toluene (1,000 ml) is added, and the mixture is filtered while hot. After cooling to lab temperature, the precipitated light-brownish crystals are sucked off. The yield is 183 g (55%), b.p. 167-169° C.

Crystallization from ethylacetate yields colorless crystalline duloxetine chloride, b.p. 170-171° C. Optical purity is 99.6% ee (CE).

Crystallization from ethylmethylketone yields colorless crystalline duloxetine chloride, b.p. 170.5-171.5° C. Optical purity is 99.6% ee (CE).

What is claimed is:
1. A method of manufacturing (S)-N-methyl-3-(1-naphthyloxy)-3-(2-thienyl)propylamine of formula I

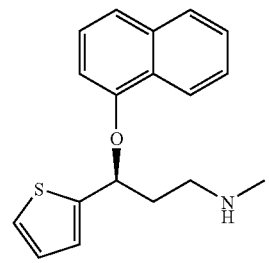

or its pharmaceutically acceptable salt, comprising (RS)-N,N-dimethyl-3-(1-naphthyloxy)-3-(2-thienyl)propylamine of formula III

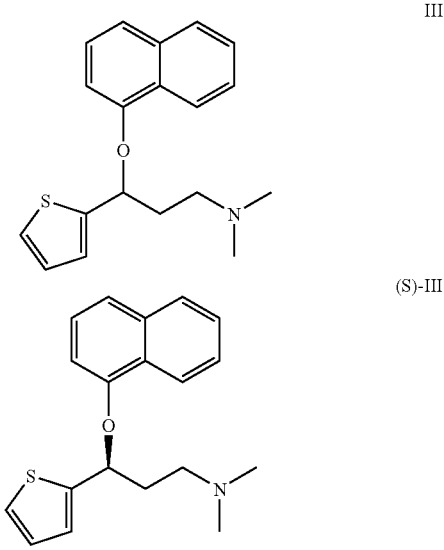

is reacted with an optically active acid, after which a crystallization is carried out of that diastereoisomer which yields, in reaction with an inorganic or organic base, (S)-N,N-dimethyl-3-(1-naphthyloxy)-3-(2-thienyl)propylamine of formula (S)-III, which is then demethylated using alkylchloroformates, followed by hydrolysis and optional conversion of the compound of formula I to its salt.

2. The method according to claim 1, wherein the compound of formula III is reacted with D-tartaric acid, the diastereoisomer (S)-N,N-dimethyl-3-(naphthyloxy)-3-(2-thienyl)propylamine-D-tartrate is crystallized from a solvent selected from cyclic ethers, $C_3$ to $C_6$ ketones or $C_1$ to $C_3$ alcohols, and (S)-N,N-dimethyl-3-(1-naphthyloxy)-3-(2-thienyl)propylamine of formula (S)-III is released via reaction with a base selected from the group of alkali metal hydroxides or carbonates.

3. The method according to claim 2, wherein crystallization of the desired diastereoisomer is performed from a solvent selected from the group including tetrahydrofuran, acetone, methanol and ethanol.

4. The method according to claim 1, wherein demethylation of (S)-N,N-dimethyl-3-(1-naphthyloxy)-3-(2-thienyl) propylamine using phenylchloroformate is performed in the mixture of toluene and diisopropylamine at 50 to 110° C., followed by a hydrolysis with an alkali metal hydroxide.

5. The method according to claim 1, wherein the starting compound of formula III, prepared via reaction of (R)-N,N-dimethyl-3-(1-naphthyloxy)-3-(2-thienyl)propylamine with a base selected from the group of alkali metal hydroxides, hydrides or alcoholates, is used.

6. The method according to claim 5, wherein the reaction is performed with potassium tert-butylate.

7. The method according to claim 5, wherein the reaction is performed with sodium methanolate.

8. The method according to claim 5, wherein the reaction is performed with potassium hydroxide.

9. The method according to claim 6, wherein DMSO is used as the solvent and after the reaction is completed, excess alcoholate is decomposed with water, after which the product is extracted with a non-polar organic solvent selected from the series of $C_5$ through $C_8$ aliphatic, cyclic or aromatic hydrocarbons.

10. The method according to claim 1, wherein the starting compound of formula III, prepared via reaction of (RS)-N,N-dimethyl-3-hydroxy-3-(2-thienyl)propylamine with 1-fluoronaphthalene in a solution of dimethylsulfoxide at 80 to 150° C. in the presence of base selected from alkali metal carbonates, hydroxides or alcoholates, is used.

11. The method according to claim 1, wherein the compound of formula I is further converted to the hydrochloride via reaction with a weak base chloride, preferably with ammonium chloride.

12. The method according to claim 7, wherein DMSO is used as the solvent and after the reaction is completed, excess alcoholate is decomposed with water, after which the product is extracted with a non-polar organic solvent selected from the series of $C_5$ through $C_8$ aliphatic, cyclic or aromatic hydrocarbons.

13. The method according to claim 8, wherein DMSO is used as the solvent and after the reaction is completed, excess alcoholate is decomposed with water, after which the product is extracted with a non-polar organic solvent selected from the series of $C_5$ through $C_8$ aliphatic, cyclic or aromatic hydrocarbons.

* * * * *